United States Patent
Gasc et al.

[11] Patent Number: 4,855,302
[45] Date of Patent: Aug. 8, 1989

[54] CERTAIN AZASPIRODECANE COMPOUNDS AND A METHOD OF INDUCING AN ANXIOLYTIC ACTIVITY

[75] Inventors: Jean-Claude Gasc, Bondy; Lucien Nedelec, Le Raincy; Daniel Humbert, Fontenay-Sous-Bois; Ana-Maria Boaventura, Courbevoie, all of France

[73] Assignee: Roussel Uclaf, Paris, France

[21] Appl. No.: 131,186

[22] Filed: Dec. 10, 1987

[30] Foreign Application Priority Data

Dec. 11, 1986 [FR]   France ................................ 86 17333

[51] Int. Cl.[4] .................... C07D 221/20; A61K 31/45; A61K 31/445
[52] U.S. Cl. ........................................ 514/278; 546/16
[58] Field of Search .......................... 546/16; 514/278

[56] References Cited

U.S. PATENT DOCUMENTS 3,635,991   1/1972   Archer ................................. 546/16

*Primary Examiner*—Alan L. Rotman
*Attorney, Agent, or Firm*—Bierman and Muserlian

[57] ABSTRACT

A compound selected from the group consisting of azaspirodecane derivatives of the formula

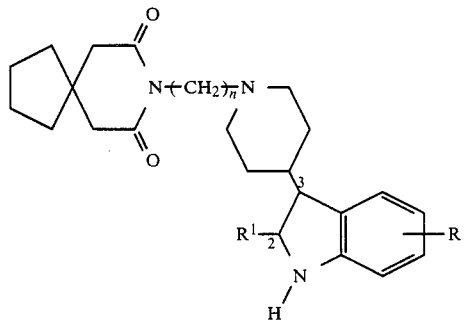

wherein R is selected from the group consisting of hydrogen, fluorine, chlorine, bromine, alkoxy of 1 to 3 carbon atoms, $-NO_2$, $-NH_2$ and $CH_3S-$ in the 4,5 or 6 position of the ring, R' is oxo or hydrogen or $-OH$ or alkyl of 1 to 3 carbon atoms and the dotted line indicates a carbon-carbon bond in the 2,3-position, n is 2,3,4 or 5 and the dotted line in the piperidyl ring is an optional carbon-carbon bond and their non-toxic, pharmaceutically acceptable acid addition salts having remarkable anxiolytic activity.

12 Claims, No Drawings

CERTAIN AZASPIRODECANE COMPOUNDS AND A METHOD OF INDUCING AN ANXIOLYTIC ACTIVITY

STATE OF THE ART

Relevant prior art includes U.S. Pat. No. 4,196,209, European patent application Ser. No. 200,322 and French BSM patent No. 6687M.

OBJECT OF THE INVENTION

It is an object of the invention to provide the novel compounds of formula I and their acid addition salts and a process for their preparation.

It is another object of the invention to provide novel anxiolytic compositions and to a novel method of inducing anxiolytic activity in warm-blooded animals.

These and other objects and advantages of the invention will become obvious from the following detailed description.

THE INVENTION

The novel compounds of the invention are selected from the group consisting of azaspirodecane derivatives of the formula

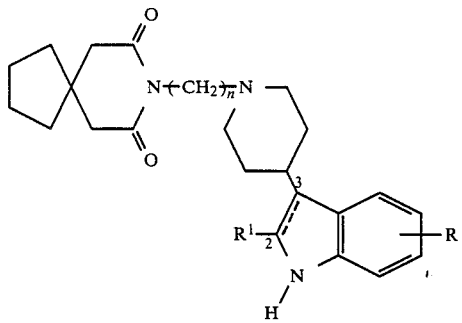

wherein R is selected from the group consisting of hydrogen, fluorine, chlorine, bromine, alkoxy of 1 to 3 carbon atoms, —NO$_2$, —NH$_2$ and CH$_3$S— in the 4,5 or 6 position of the ring, R' is oxo or hydrogen or —OH or alkyl of 1 to 3 carbon atoms and the dotted line indicates a carbon-carbon bond in the 2,3-position, n is 2,3,4 or 5 and the dotted line in the piperidyl ring is an optional carbon-carbon bond and their non-toxic, pharmaceutically acceptable acid addition salts.

In the compounds of formula I, the alkoxy of 1 to 3 carbon atoms may be propoxy or ethoxy but preferably is methoxy and alkyl of 1 to 3 carbon atoms may be n-propyl, isopropyl or ethyl but preferably is methyl.

Examples of suitable acids for the formation of the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzene sulfonic acid and p-toluene sulfonic acid and arylcarboxylic acids such as benzoic acid.

Among the preferred compounds of formula I are those where n is 4 and those wherein the dotted line in piperidyl is a carbon-carbon bond and their non-toxic, pharmaceutically acceptable acid addition salts. A preferred compound of the invention 8-[4-{4-(5-methoxy-1H-indol-3-yl)-1,2,3,6-tetrahydro-1-pyridinyl]-butyl}-8-azaspiro[4,5]decane-7,9-dione and its non-toxic, pharmaceutically acceptable acid addition salts.

The novel process of the invention for the preparation of the compounds of formula I comprises reacting a compound of the formula

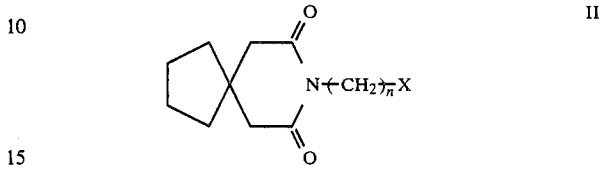

wherein n has the above definition and X is selected from the group consisting of chlorine, bromine, iodine and —OH with an indole of the formula

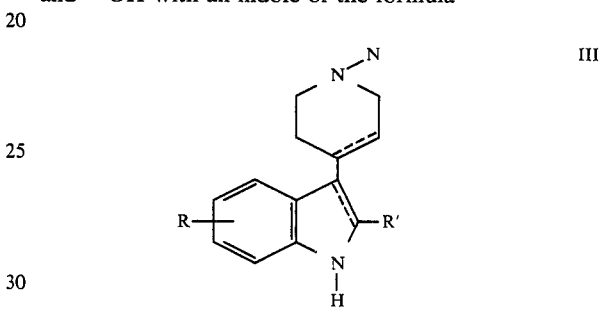

wherein R, R' and the dotted line have the above definition to obtain the corresponding compound of formula I which may be isolated and optionally salified.

In a preferred mode of the process of the invention, the reaction is effected in the presence of a mineral basic condensation agent such as alkali metal carbonates or bicarbonates like sodium or potassium carbonate or bicarbonate or alkali metal hydroxides such as potassium hydroxide or sodium hydroxide or an organic basic agent such as pyridine, triethylamine or an alkali metal alcoholate such as sodium ethylate when X is chlorine, bromine or iodine. When X is hydroxy, the condensation agent may be N,N'-carbonyldiimidazole or dicyclohexylcarbodiimide.

The compounds of formula II are known and are described, for example, in French Pat. Nos. 2,362,628; 2,444,678; 2,460,946; 2,421,899; 2,444,679; 2,458,550; 2,470,128 and 2,477,415. The compounds of formula III are also known and are described in French BSM Pat. No. 6687M, for example.

The compounds of formula I wherein R' is keto may be prepared by reacting the corresponding 2-indolinone with 4-piperidone with the amine being protected by benzyl in the presence of ammonia followed by catalytic hydrogenation such as in the presence of palladium to obtain the desired compound of claim 1.

The compounds of formula I have a basic character and the acid additions salts may be prepared by reacting substantially stoichiometric amounts of the compound of formula I and the desired acids with or without isolation of the base.

The novel anxiolytic compositions of the invention are comprised of an anxiolytically effective amount of at least one compound of formula I and their non-toxic, pharmaceutically acceptable acid addition salts and an inert pharmaceutical carrier. The compositions may be in the form of tablets, dragees, gelules, granules, suppositories and injectable solutions or suspensions.

Examples of the inert carrier or excipient are talc, arabic gum, lactose, starch, magnesium stearate, cocao butter, aqueous and non-aqueous vehicles, fatty bodies of animal or vegetable origin, paraffin derivatives, glycols, diverse wetting agents, dispersants and emulsifiers and preservatives.

The compositions are useful for the treatment of anxiety states such as chronic anxiety associated with or without insommia or behavior problems, anguish in adults or infants, or as a complement in the treatment with neuroleptics or antidepressants in psychotic or depressive states.

The novel method of inducing anxiolytic activity in warm-blooded animals, including humans, comprises administering to warm-blooded animals an anxiolytically effective amount of at least one compound of formula I and their non-toxic, pharmaceutically acceptable acid addition salts. The compounds may be administered orally, rectally or parenterally and the usual daily dose is 0.01 to 6.7 mg/kg depending on the condition treated, the method of administration and the specific compound. For example, the compound of Example 4 may be administered at a daily dose 0.03 to 3 mg/kg to treat chronic anxiety.

In the following examples there are described several preferred embodiments to illustrate the invention. However, it should be understood that the invention is not intended to be limited to the specific embodiments.

EXAMPLE 1

8-[4-{4-(5-methoxy-1H-indol-3-yl)-1-piperidinyl}-butyl]-8-azaspiro[4,5]decane-7,9-dione A mixture of 2.3 g of 5-methoxy-3-(4-piperidinyl)-1H-indole, 2.58 g of 8-[4-chlorobutyl-8-azaspiro[4,5]decane-7,9-dione, 2.12 g of sodium carbonate, 150 mg of sodium iodide and 50 ml of butanone was refluxed under an inert atmosphere with stirring for 20 hours and after another 1.29 g of the dione were added. Reflux was continued for 6 hours. The mixture was filtered and washed with acetone and the filtrate was evaporated to dryness. The residue was crystallized from 60% ethanol to obtain 3.4 g of 8-[4-{4-(5-methoxy-1H-indol-3-yl)-1-piperidinyl}-butyl]-8-azaspiro[4,5]decane-7,9-dione melting at $\approx 150°$ C.

6.49 g of the base were added to 40 ml of methylene chloride and 2 ml of ethanolic 7.4N hydrochloric acid were added. The product was dried and taken up in ethyl acetate. The precipitate was crystallized from absolute ethanol to obtain 5.78 g of the hydrochloride salt melting at $\approx 209°$ C.

| UV Spectrum (ethanol): | | | |
|---|---|---|---|
| Inflex. toward | 221 nm | $E_1^1 = 625$ | $\epsilon = 30{,}500$ |
| Max. at | 276 nm | $E_1^1 = 121$ | $\epsilon = 5{,}900$ |
| Max. at | 298 nm | $E_1^1 = 99$ | $\epsilon = 4{,}800$ |
| Max. at | 308 nm | $E_1^1 = 73$ | $\epsilon = 3{,}550$ |

EXAMPLE 2

8-[4-{4-(1H-indol-3-yl)-1,2,3,6-tetrahydro-1-pyridinyl}-butyl]-8-azaspiro[4,5]decane-7,9 dione Using the procedure of Example 1, 3-(1,2,3,6-tetrahydro-pyridin-4-yl)-1H-indole was reacted to obtain 8-[4-{4-(1H-indol-3-yl)-1,2,3,6-tetrahydro-1-pyridinyl}-butyl]-8-azaspiro[4,5]decane-7,9-dione and its hydrochloride.

| UV Spectrum (ethanol) of hydrochloride | |
|---|---|
| Max. at 217 nm | $E_1^1 = 688$ |
| Max. at 260 nm | $E_1^1 = 337$ |
| Max. at 282 nm | $E_1^1 = 234$ |
| UV Spectrum (ethanol −0.1 N HCl) of hydrochloride | |
| Max. at 217 nm | $E_1^1 = 707$ |
| Max. at 261 nm | $E_1^1 = 343$ |
| Max. at 282 nm | $E_1^1 = 232$ |

EXAMPLE 3

8-[4-{4-(5-chloro-1H-indol-3-yl)-1,2,3,6-tetrahydro-1-pyridinyl}-butyl]-8-azaspiro[4,5]decane-7,9-dione Using the procedure of Example 1, 5-chloro-3-(1,2,3,6-tetrahydropyridinyl-4-1H-indole was reacted to obtain 8-[4-{4-(5-chloro-1H-indol-3-yl)-1,2,3,6-tetrahydro-1-pyridinyl}-butyl]-8-azaspiro[4,5]decane-7,9-dione and its hydrochloride.

| UV Spectrum (ethanol): free base | | |
|---|---|---|
| Max. at 251 nm | $E_1^1 = 408$ | $\epsilon = 18{,}500$ |
| Max. at 261 nm | $E_1^1 = 401$ | $\epsilon = 18{,}200$ |
| Max. at 289 nm | $E_1^1 = 130$ | $\epsilon = 5{,}900$ |
| UV Spectrum (ethanol − 0.1 N HCl): free base | | |
| Inflex at 256 nm | $E_1^1 = 372$ | |
| Max. at 262 nm | $E_1^1 = 409$ | $\epsilon = 18{,}600$ |
| Max. at 288 nm | $E_1^1 = 184$ | $\epsilon = 8{,}350$ |
| UV Spectrum (ethanol): hydochloride | | |
| Max. at 216 nm | $E_1^1 = 583$ | $\epsilon = 28{,}600$ |
| Max. at 229 nm | $E_1^1 = 565$ | $\epsilon = 27{,}700$ |
| Inflex towards 253 nm | $E_1^1 = 330$ | |
| Max. at 262 nm | $E_1^1 = 360$ | $\epsilon = 17{,}700$ |
| Max. at 288 nm | $E_1^1 = 166$ | $\epsilon = 8{,}100$ |
| Inflex. towards 295 nm | $E_1^1 = 140$ | |
| UV Spectrum (ethanol −0.1 N HCl): hydrochloride | | |
| Max. at 217 nm | $E_1^1 = 588$ | $\epsilon = 20{,}000$ |
| Max. at 229 nm | $E_1^1 = 575$ | $\epsilon = 28{,}200$ |
| Inflex. towards 256 nm | $E_1^1 = 338$ | |
| Max. at 262 nm | $E_1^1 = 370$ | $\epsilon = 18{,}100$ |
| Max. at 286 nm | $E_1^1 = 163$ | $\epsilon = 8{,}000$ |
| Inflex. towards 295 nm | $E_1^1 = 145$ | |

EXAMPLE 4

8-[4-{4-(5-methoxy-1H-indol-3-yl)-1,2,3,6-tetrahydro-1-pyridinyl}-butyl]-8-azaspiro[4,5]decane-7,9-dione Using the procedure of Example 1, 5-methoxy-3-(1,2,3,6-tetrahydro-pyridin-4-yl)-1H-indole was reacted to obtain 8-[4-{4-(5-methoxy-1H-indol-3-yl)-1,2,3,6-tetrahydro-1-pyridinyl}-butyl]-8-azaspiro[4,5]decane-7,9-dione melting at $\approx 200°$ C.

EXAMPLE 5

8-[4-{4-(2,3-dihydro-2-oxo-1H-indol-3-yl)-piperidin-1-yl}-butyl]-8-azaspiro[4,5]decane-7,9-dione Using the procedure of Example 1, 3-(piperidin-4-yl)-2,3-dihydro-3-oxo-1H-indole was reacted in methylisobutyl ketone at reflux for 4 hours to obtain 8-[4-{4-(2,3-dihydro-2-oxo-1H-indol-3-yl)-piperidin-1-yl}-butyl]-8-azaspiro[4,5]decane-7,9-dione melting at $\approx 175°$ C.

EXAMPLE 6

8-[4-{4-(4-methoxy-1H-indol-3-yl)-1,2,3,6-tetrahydro-1-pyridinyl}-butyl]-8-azaspiro[4,5]decane-7,9-dione Using the procedure of Example 1, 4-methoxy-3-(1,2,3,6-tetrahydropyridin-4-yl)-1H-indole succinide was reacted with potassium carbonate as the condensation agent and chlorobenzene as the solvent to obtain 8-[4-{4-(4-methoxy-1H-indol-3-yl)-1,2,3,6-tetrahydro-1-pyridinyl}-butyl]-8-azaspiro[4,5]decane-7,9-dione melting at $\simeq 153°$ C.

EXAMPLE 7

8-[4-{4-(6-methoxy-2-methyl-1H-indol-3-yl)-piperidin-1-yl}-butyl]-8-azaspiro[4,5]decane-7,9-dione Using the procedure of Example 6, the product of Step B was reacted to obtain 8-[4-{4-(6-methoxy-2-methyl-1H-indol-3-yl)-piperidin-yl}-butyl]-8-azaspiro[4,5]decane-7,9-dione melting at $\simeq 75°$ C.

Preparation of (piperydyl-4)-3-indoline-2-one

STEP A

[benzyl-1-piperidylene-4]-3-indoline-2-one

Ammonia was bubbled for one hour into a solution of 50 g of 2-indolinone and 73 g of N-benzyl-4-piperidone in 1,050 ml of ethanol at 25° to 30° C. and the mixture was heated at 80° C. to distill 700 ml of ethanol. The mixture was cooled to 20° C. and 300 ml of water were slowly added with stirring. The mixture was vacuum filtered and the product was washed and dried to obtain 100.5 g of [benzyl-1-piperidylene-4]-3-indoline-2-one melting at $\simeq 220°$ C.

STEP B (piperidyl-4)-3-indoline-2-one

A mixture of 50 g of the product of Step A, 500 ml of methanol and 5 g of 10% palladized carbon was hydrogenated for 16 hours and was then filtered. The filtrate was evaporated to dryness and the residue was crystallized from benzene to obtain 21.3 g of (piperidyl-4)-3-indoline-2-one melting at $\simeq 160°$ C.

EXAMPLE 8

Tablets were prepared containing 50 mg of the product of Example 4 or 100 mg of the hydrochloride product of Example 2 and sufficient excipient of lactose, starch, talc and magnesium stearate for a final tablet weight of 200 mg.

PHARMACOLOGICAL DATA

A. Stair Test

The apparatus and protocole used was that described by Thiebot et al [Psychopharmacolgia (Berlin), Vol. 31 (1973), p. 77]. The test was effected on groups of natural rats which were individually placed in the enclosure 30 minutes to one hour after the intraperitoneal or oral administration of the test compound. The number of straightings effected and the number of steps climbed by the animals in 3 minutes were counted. The compounds of Examples 2, 4, and 5 at a dose of 10 mg/kg (oral), 5 mg/kg (oral) and 0.5 mg/kg (intraperitoneal), respectively, diminished significantly the number of straightings without noticable modification of the number of steps climbed by the animals. They presented a good anxiolytic activity.

B. Test of 4 plates

The apparatus (Apelab) and the test procedure for mice described by Boissier et al [European J. Pharmacol. Vol. 4 (1968), p. 14] was used with rats. The plates were connected to a stimulator (U. Sachs, Roucaire) to deliver electric shocks of 120 volts every 0.5 seconds. The tests were conducted on groups of 8 rats 20 minutes or 1 hour after oral or intraperitoneal administration of the test compound. Each animal was individually placed in the apparatus and after 15 seconds of free exploration, it was subjected to an electric shock each time it passed from one plate to another with a minimum of 3 seconds observed between two shocks. The number of shocks delivered in 3 minutes were counted and the results were compared with controls animals by the Dunnett test. The oral or intraperitoneal dose which significantly increased the number of shocks were counted and the results are reported in the following Table.

| Product of Example | Dose in mg/kg |
|---|---|
| 2 | 20 (oral) |
| 3 | 10 (oral) |
| 4 | 5 (intraperitoneal) |

The tested products showed a notable anxiolytic activity.

C. Acute toxicity test

The lethal dose $LD_0$ was determined by tests using mice receiving the test compounds orally. The $LD_0$ is the maximum dose at which no deaths occured in 8 days and the results are reported in the following Table.

| Product of Example | $DL_0$ in mg/kg |
|---|---|
| 1 | 200 |
| 2 | 400 |
| 3 | 400 |
| 4 | 400 |
| 5 | 100 |

Various modifications of the products and methods of the invention may be made without departing from the spirit or scope thereof and it should be understood that the invention is to be limited only as defined in the appended claims.

What we claim is:

1. A compound selected from the group consisting of azaspirodecane derivatives of the formula

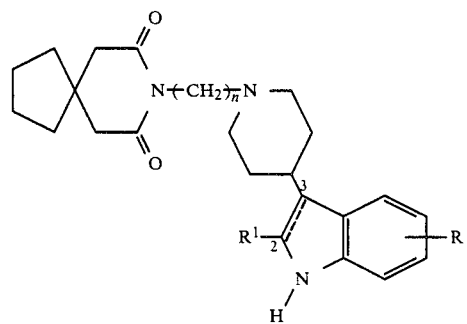

wherein R is selected from the group consisting of hydrogen, fluorine, chlorine, bromine, alkoxy of 1 to 3 carbon atoms, —NO₂, —NH₂ and CH₃S— in the 4,5 or 6 position of the ring, R' is oxo or hydrogen or —OH or alkyl of 1 to 3 carbon atoms and the dotted line indicates a carbon-carbon bond in the 2,3-position, n is 2,3,4 or 5 and the dotted line in the piperidyl ring is an optional carbon-carbon bond and their non-toxic, pharmaceutically acceptable acid addition salts.

2. A compound of claim 1 wherein n is 4.

3. A compund of claim 1 wherein the dotted line in the pyperidyl ring is a carbon-carbon bond.

4. A compound of claim 1 wherein the compound is selected from the group consisting of 8-[4-{4-(5-methoxy-1H-indol-3-yl)-1,2,3,6-tetrahydro-1-pyridinyl}-butyl]-8-azaspiro[4,5]decane-7,9-dione and its non-toxic, pharmaceutically acceptable acid addition salts.

5. An anxiolytic composition comprising an anxiolytically effective amount of a compound of claim 1 and an inert pharmaceutical carrier.

6. A composition of claim 5 wherein n is 4.

7. A composition of claim 5 wherein the dotted line in the pyperidyl ring is a carbon-carbon bond.

8. A composition of claim 5 wherein the active compound is selected from the group consisting of 8-[4-{4-(5-methoxy-1H-indol-3-yl)-1,2,3,6-tetrahydro-1-pyridinyl}-butyl]-8-azaspiro[4,5]decane-7,9-dione and its non-toxic, pharmaceutically acceptable acid addition salts.

9. A method of inducing anxiolytic activity in warm-blooded animals comprising administering to warm-blooded animals an anxiolytically effective amount of a compound of claim 1.

10. The method of claim 9 wherein n is 4.

11. The method of claim 9 wherein the dotted line in the pyperidyl ring is a carbon-carbon bond.

12. The method of claim 9 wherein the active compound is selected from the group consisting of 8-[4-{4-(5-methoxy-1H-indol-3-yl)-1,2,3,6-tetrahydro-1-pyridinyl}-butyl]-8-azaspiro[4,5]decane-7,9-dione and its non-toxic, pharmaceutically acceptable acid addition salts.

* * * * *

UNITED STATES PATENT AND TRADEMARK OFFICE
CERTIFICATE OF CORRECTION

PATENT NO. : 4,855,302

DATED : Aug. 8, 1989

INVENTOR(S) : JEAN-CLAUDE GASC et al

It is certified that error appears in the above-identified patent and that said Letters Patent is hereby corrected as shown below: On the title page:

Col.      fomula I     Abstract

[57]

1   Formula 1   2

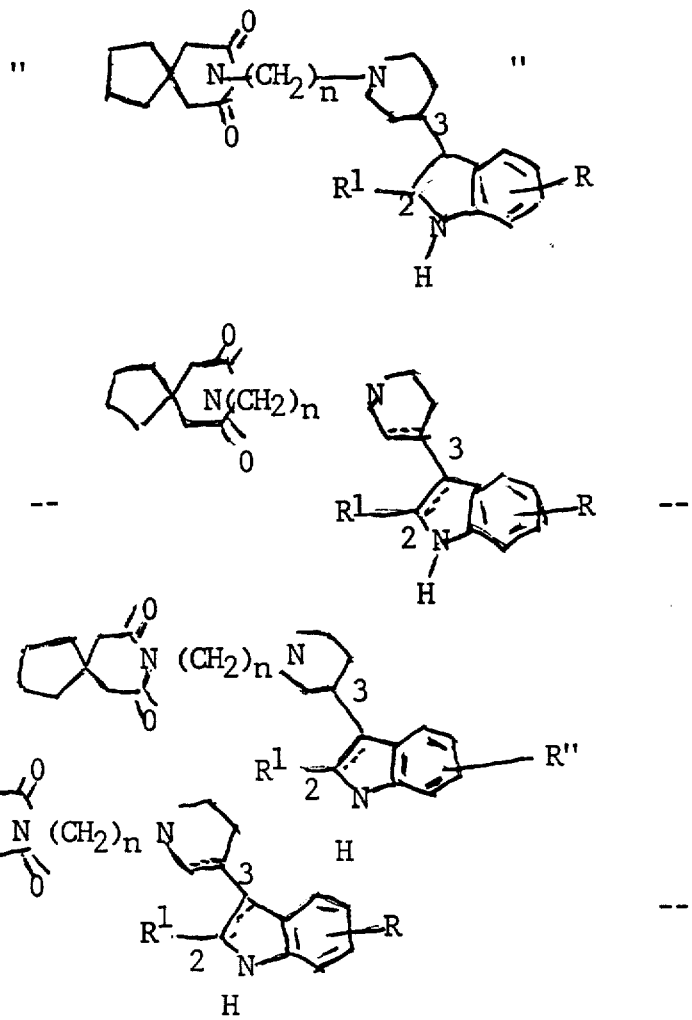

UNITED STATES PATENT AND TRADEMARK OFFICE
CERTIFICATE OF CORRECTION

PATENT NO. : 4,855,302

DATED : Aug. 8, 1989

INVENTOR(S) : JEAN-CLAUDE GASC et al

It is certified that error appears in the above-identified patent and that said Letters Patent is hereby corrected as shown below:

| Col. | Line | |
|---|---|---|
| 3 | 47 | " 150°C" should be -- 150°C-- |
| 3 | 53 | " 209°C should be -- 209°C-- |
| 6 | Formula I | Same as Abstract and Invention |
| 7 | line 7 | "their" should be --or a-- |
| 7 & 8 | Claims 4, 8 and 12 line 5 | "its non-toxic, pharmaceutically acceptable acid addition salts" should be --a non-toxic, pharmaceutically acceptable acid addition salts thereof-- |
| 7 | line 7 | "salts" should be --salt-- |
| 7 | line 10 | "pyperidyl" should be --peperidyl-- |
| 7 | line 5 | "its non-toxic, pharmaceutically acceptable acid addition salts" should be --a non-toxic, pharmaceutically acceptable acid addition salt thereof-- |

Signed and Sealed this

Twenty-fourth Day of April, 1990

Attest:

HARRY F. MANBECK, JR.

*Attesting Officer*    *Commissioner of Patents and Trademarks*